(12) United States Patent
Chinnock et al.

(10) Patent No.: US 7,187,442 B2
(45) Date of Patent: Mar. 6, 2007

(54) POLARIZED OPTICAL PROBES

(75) Inventors: Randal B. Chinnock, Sturbridge, MA (US); Jeffrey S. Melanson, Sturbridge, MA (US)

(73) Assignee: Optimum Technologies, Inc., Southbridge, MA (US)

(*) Notice: Subject to any disclaimer, the term of this patent is extended or adjusted under 35 U.S.C. 154(b) by 397 days.

(21) Appl. No.: 10/835,747

(22) Filed: Apr. 30, 2004

(65) Prior Publication Data

US 2005/0243314 A1    Nov. 3, 2005

(51) Int. Cl.
*G01J 4/00* (2006.01)
(52) U.S. Cl. ...................................... 356/364
(58) Field of Classification Search ............ None
See application file for complete search history.

(56) References Cited

U.S. PATENT DOCUMENTS 4,286,843 A * 9/1981 Reytblatt .................... 359/489

2002/0191185 A1 * 12/2002 Rotter et al. ................. 356/369

* cited by examiner

*Primary Examiner*—Tu T. Nguyen
(74) *Attorney, Agent, or Firm*—Brian M. Dingman, Esq.; Mirick, O'Connell, DeMallie & Lougee

(57) ABSTRACT

A variably-polarizing optical probe assembly. The assembly includes an optical probe having one or more optical light delivery channels that emit incident light from the sample end of the probe toward a sample being investigated, and one or more optical light-receiving channels that receive incident light from the sample. A variably-polarizing substrate assembly is coupled to the sample end of the probe. The substrate assembly includes an optically transmitting substrate and one or more discrete polarizer areas on a face of the substrate, each such polarizer area defining a polarization orientation, with the polarizer areas together defining one or more different polarization orientations. The substrate assembly is arranged relative to the probe such that one polarizer area covers at least one light delivery channel and one polarizer area covers at least one light-receiving channel.

20 Claims, 5 Drawing Sheets

10

POLARIZED OPTICAL PROBES

GOVERNMENT RIGHTS

This invention was made with Government support under (Grant Number 1 R43 CA103083-01) awarded by the National Institutes of Health (NIH). The Government has certain rights in the invention. The inventor is an employee of the assignee, Optimum Technologies, Inc. of Southbridge, Mass.

FIELD OF THE INVENTION

This invention relates to polarized optical probes.

BACKGROUND OF THE INVENTION

Methods of Optical Analysis

Photons from the ultraviolet, optical, and infrared portions of the electromagnetic spectrum have been used for over 100 years to investigate the properties of matter. These techniques, hereinafter referred to as "methods of optical analysis", include but are not limited to Raman spectroscopy, infrared (IR) spectroscopy, atomic absorption spectroscopy, diffuse reflectance spectroscopy, fluorescence spectroscopy, photoluminescence spectroscopy, and elastic scattering spectroscopy.

In Raman spectroscopy, a sample is irradiated with a substantially monochromatic light source. A small percentage of the incident photons absorbed by the sample are instantaneously re-emitted at slightly different wavelengths. These shifts in wavelength, referred to as Stokes or anti-Stokes shifts, result from changes in the rotational and vibrational states of the constituent molecules. The emitted spectra, captured in a backscattered configuration and analyzed with the spectrometer, reveal very specific information about the chemistry and structure of the sample, particularly information related to carbon-carbon bonds.

IR spectroscopy is similar to Raman, but operates at longer wavelengths. The method is sensitive to functional group vibrations especially OH stretch in water, and is good for studying the substituents on organic molecules. Also, the method can use the unique collection of absorption bands to confirm the identity of a pure compound or to detect the presence of specific impurities Fluorescence spectroscopy is similar to Raman spectroscopy, in that a sample is irradiated with a substantially monochromatic light source and the re-emitted spectra is captured and analyzed by a spectrometer. However, in the case of fluorescence the emitted spectrum is derived from certain electronic transitions in the sample's constituent molecules. This spectrum is broader and more intense than Raman spectra, lacks Raman's fine structure, and occurs over an extended time frame. Fluorescence spectroscopy is used to determine the chemical constituents of a sample.

In diffuse reflectance spectroscopy (DRS), a broadband light source irradiates a mostly opaque sample. Certain wavelengths of light are selectively absorbed by the sample, and some are scattered. A spectrometer configured to capture backscatter analyzes the spectrum of the scattered rays. "Dips" in the spectrum, caused by absorption in the sample, reveal information about the molecular content of the sample.

In DRS, scattered photons captured by the spectrometer may have undergone elastic or inelastic scattering, or both. Elastic scattering spectroscopy (ESS) is similar to DRS, except that the geometry of the optical system is controlled so that only rays that have undergone high-angle elastic scattering are captured by a spectrometer. Mie scattering theory is then used to analyze the spectra. These spectra reveal information about the size of the scatterers, their index of refraction, the average distance between scatterers, and ranges of values on these measures. This technique has been used to analyze industrial materials such as slurries containing liquids and suspended particles. It has also been used to assess biological tissues. In this case, the ESS spectrum reveals the size of intracellular components such as nuclei and mitochondria. Enlargement of these components above normal levels may indicate a disease state such as cancer.

In atomic absorption spectroscopy, a broadband light source and a spectrometer are arranged in an "opposed" configuration (facing each other) to measure gas-phase atoms. Since the samples of interest are usually liquids or solids, the analyte atoms or ions must be vaporized in a flame or graphite furnace in order to be analyzed. The atoms absorb ultraviolet or visible light and make transitions to higher electronic energy levels. The analyte concentration is determined from the amount of absorption as the light passes through the vaporized sample. This technique is capable of detecting very small concentrations of atoms or molecules in a sample.

Fourier transform (FT) techniques may alternatively be used with many of the optical analysis methods described above. FT techniques convert a time domain measurement to a frequency domain measurement, or vice versa. Instruments employing FT basically reveal the same information about a sample as a comparable instrument without FT, but an FT instrument may be optimized for higher resolution, higher speed, higher sensitivity, or other parameters.

The Use of Polarization in Optical Analysis Techniques

The term "polarization" refers to the spatial orientation of the electromagnetic field associated with each photon. Most naturally-occurring and manmade light sources produce photons with random polarization states. Lasers are generally highly polarized. In all of the optical analysis methods described above, non-polarized light may be used. However, with some of these techniques, the use of polarized light may enable benefits such as higher sensitivities, improved signal-to-noise ratios (SNRs) or additional capabilities.

For example, polarized atomic absorption spectroscopy systems such as the Hitachi Z-5000 offer lower detection limits with a smaller, simpler instrument design compared to non-polarized instruments.

Polarized Raman spectroscopy is used, for example, to determine the secondary and tertiary structures of membrane proteins in biological samples. By studying these aligned proteins with polarized Raman spectroscopy, additional data about the orientation of the bond-polarizability tensors with respect to the known polarization direction of the laser is obtained. This information is combined with molecular models to infer details about the structure of the protein.

In the materials science field, optical strain gauges may also employ polarized Raman. Sensors are constructed by embedding carbon nanotubes in a polymer. Polarized Raman analysis is very sensitive to the strain transferred from the matrix to the nanotubes.

External Reflection Spectroscopy (IRRAS) is used to examine thin films on mirror-like substrates such as coatings and adhesives on metal surfaces. Using a grazing angle technique, the beam makes a high-angle reflection of approximately 88° from the sample and is polarized in the plane of incidence (p-polarization). Polarization sensitivity makes IRRAS useful in determining the orientation of molecules in relation to the metal.

In the polarized variant of ESS (PESS), a polarized broadband source is used to irradiate a sample such as biological tissue. Instead of a single optical channel for measuring the backscattered light in ESS, two channels are used in PESS. One channel is polarized with the same spatial orientation as the source channel, while the other channel is cross-polarized. Since the polarization of backscattered photons depends on the number of scattering events the photon has undergone, and their subtended scattering angle, this detection method collects photons mostly from a well-defined region of the tissue and filters out photons scattered from underlying and surrounding tissue. This enables measurements with high spatial specificity and high signal-to-noise ratio. Recent clinical studies have demonstrated the utility of PESS for the analysis of the surface layers of human tissues lining the outside of the body and body canals (epithelia). Carcinomas originate in epithelial layers, so sampling of this layer independent of the sub-epithelial layers enables the detection of atypical tissues at the earliest stages of growth. ESS and PESS investigations are currently being conducted in many parts of the body, including the gastrointestinal tract (oral cavity, esophagus, stomach, intestines), mammary ducts, bladder, urethra, cervix, and skin.

Fiberoptic Sampling Probes

In many applications, it is desirable to measure a sample in situ, rather than removing a sample from its original location for analysis in a laboratory. Examples in the medical field include measurements of human or animal tissue in vivo, either on the surface of the body, subsurface using a percutaneous technique, or deep inside the body using an endoscope. Pharmaceutical and cosmetic applications include measurements of powders, slurries, suspensions, and solids. Environmental applications include field measurements of water in lakes and streams, and gases in smokestack emissions. Industrial applications include process control measurements in locations such as chemical plants, oil refineries, food processing plants, breweries, and fuel depots. Public safety, security, and forensic applications include detection of explosives residue, illegal drugs, and biohazards such as biological warfare agents, toxic chemicals, and microbial contamination.

In a number of these applications, physical access to the sample is limited. For example, in a lake it may be desired to take a measurement at a depth of 2 meters. In the body, a sample may be required deep in the esophagus. In a cosmetics factory, a sample may be required of a slurry inside a vat or flowing in a pipe. For many of these applications, it is not possible to bring the analytical instrument to the sample. Instead, fiberoptic probes provide the optimal means of conveying light from the instrument to the sample, and/or from the sample to the instrument. Fiberoptic probes are efficient conductors of broadband light, are immune to electromagnetic interference, can be very long (up to hundreds of meters in length), and may be constructed to be flexible, with very small cross sections that can fit into tiny spaces.

Polarized Fiberoptic Probes

Implementing polarized detection in fiberoptic probes has historically had its limitations. Following is a discussion of issues pertaining to the use of fiberoptic probes for Polarized ESS (PESS). However, the main points of the discussion are also applicable to the other optical analysis methods discussed above, and are intended to illustrate the general case.

There are several design difficulties in trying to make small-diameter PESS probes suitable for certain applications, especially in the medical field for needle- or endoscopic-delivery in-vivo.

In order for PESS to work properly, broadband polarized light must be delivered to a sample, and two detection channels must conduct broadband light to spectrometers for analysis of the scattering. The two detection channels must have orthogonal polarizations with a high contrast ratio (at least 10:1, and preferably >100:1). Achieving high contrast detection of two polarization modes over broad passbands is the principal challenge. For the PESS application, "broadband" means a passband of about 600 nm. For other applications, "broadband" may mean as little as 20 nm.

Fabricating polarized optical probes may be approached in two ways. FIG. 1 shows the first approach. An analysis instrument 1 is optically coupled 2 to an optical probe 3. The probe contains one delivery channel 4 and two collection channels 5 and 6. The probe is in optical communication 7 with tissue or another type of sample 8. The polarizers 9 are placed between the probe 3 and instrument 1, and polarize the light as it is transmitted. This is the easier approach because the polarizers are inside the analysis instrument instead of being part of the probe, and so there is little constraint on their size or cost. However, with this arrangement the optical channels 4, 5 and 6 must maintain the polarization of the incident light as the light propagates along the length of the probe 3. If the channels are constructed using conventional optical fiber, polarization is lost, invalidating the measurement. While polarization-maintaining fibers exist, they only offer acceptable performance over a maximum passband on the order of 20 nm. They are thus unsuitable for optical analysis methods employing broadband light.

The second approach is to place the polarizers at the sample end of the probe. This is advantageous, as the light is polarized as it exits the delivery fiber on its way to the sample, and the scattered light is polarized as it enters the detection fibers. Since only light of the correct polarization enters each detection channel, loss of polarization as the light propagates along the length of the channel does not affect the measurement. This allows the probe to be constructed, for example, with commercially available broadband fiber (such as silica-clad-silica).

Nevertheless, this approach presents a number of difficulties. First, for the PESS application, as the probe is mainly intended for measurements of epithelial tissues, it is desirable to confine the sensing volume to the first 300 microns of tissue depth. This constrains the optical geometry of the distal tip—the delivery and collection fibers must be separated by no more than a few hundred microns, and their end faces must be in very close proximity to the tissue. To eliminate crosstalk caused by Fresnel reflections (i.e., light leakage from one optical channel to another caused by reflections from optical surfaces), any polarizer placed between the fibers and the tissue must have a thickness that is less than the spacing between the fibers. This puts further constraints on the size and shape of the polarizers, as well as the fibers.

To be commercially viable, a single-use medical probe must also have a low manufacturing cost. This eliminates the use of any fabricated parts that have a high labor content. If the probe is reusable, the manufacturing cost can be higher, but the probe must withstand high temperature sterilization by steam autoclave. This puts additional constraints on materials, adhesives and coatings.

None of the conventional polarizer technologies has the necessary characteristics for this application. Dielectric thin film cube beamsplitters rely on the difference in the reflectance of S and P polarization states with angle. This means that the surface on which the coating is deposited must be mounted at an angle to the optical axis. This is typically achieved by depositing the polarizing coating onto a 45° surface inside a cube beamsplitter. Unpolarized light is split into S and P components at the 45° surface. However, placing a tiny cube at the sample end of a small diameter probe presents several difficulties. First, because the ray bundles exiting the delivery channels diverge, the cube must be significantly larger than the channel diameter, driving the overall probe size up. This makes its use infeasible in certain applications, especially certain parts of the body. Second, the cross-polarized collection channel requires the use of a second cube that is rotated 90° to the aligned cube. This complicates the design and increases the probe size further; probes using dielectric thin film cube beamsplitters are typically in the range of 1"–4" in diameter. Third, in order to prevent Fresnel reflections from the sample side of the beamsplitter cubes, those optical surfaces must either be tilted or coated with a high efficiency anti-reflection coating, further increasing complexity and cost. The use of cube beamsplitters thus does not lead to a commercially-viable probe manufacturing cost in any volume Dichroic Sheet Polarizers have also been used by some researchers to construct fiberoptic probes. "Dichroism" is selective absorption of one polarization plane over the other during transmission through a material. Sheet-type dichroic polarizers are generally manufactured using films of organic materials. The film is stretched, aligning molecules into a birefringent geometry, and then dyed. The dye molecules selectively attach themselves to aligned polymer molecules, so that absorption is high in one plane and weak in the other. The stretched film is then bonded to a transparent substrate or sandwiched between a pair of sheets (glass, plastic, fused silica, etc.) to stabilize it and protect it from the environment. The transmitted beam is linearly polarized. Polarizers made of such material are very useful for low-power and visual applications. The main advantages of this type of polarizer are good performance vs. angle of incidence and thin substrate thickness. However, there are several problems with using dichroic polarizers for fiberoptic probes. First, none of the organic compounds used in these polarizers remain stable when exposed to the temperatures required for steam autoclave (>120° C.). Since steam autoclaving is the most common method of sterilizing reusable medical devices, this is a major impediment to commercialization. Second, none of the dichroic polarizers have the desired spectral bandwidth. Some are optimized for the UV, some for the visible, but none for both. This limits the clinical utility of the probe. Third, though the dichroic sheet polarizers have the shortest optical path of any polarizer, the commercially available ones are still too thick (~200 microns—Polaroid Corp.). This results in Fresnel reflections from the sample side of the polarizer. Fourth, it is difficult to cut, handle, and bond such a tiny disk of filter material to the end of a fiber probe. Because the films have been stretched in one axis, when mounted on thin substrates, these polarizers curl very strongly, contributing to difficulties in handling. This is exacerbated by the fact that tiny pieces of the film must be mounted with their polarization axes orthogonal to each other. Fifth, since the bonding area is so small, the polarizers could detach, especially if prone to curling, and especially if the probe is used multiple times. If they detached in-vivo, this could pose a health hazard.

Birefringent polarizers have also been considered, but the polarizing crystals are typically in the range of several millimeters thick, making them impractical for small diameter probes. They are also too fragile to be placed at the distal end of a probe, and are too expensive for typical commercial applications.

Wire grid array polarizers use a periodic series of parallel wires etched or deposited onto a substrate, as described in U.S. Pat. No. 6,122,103. This array passes one polarization mode and reflects the orthogonal one. It offers very high transmission, high extinction, large acceptance angle, high temperature tolerance, and may be used normal or inclined to the optical axis. Semiconductor lithographic methods are used to form the array of wires on the transparent substrate. However, commercial wire grid polarizers are typically deposited on substrates several mm thick. Using such a thick polarizer at the distal end of a small diameter probe would result in unacceptable performance due to Fresnel reflections. Also, wire grid polarizers have been used mainly in the display industry. Thus, the substrates typically have a large area, all with the same polarization orientation. This arrangement is called a "sheet polarizer".

In sum, none of the existing polarizer technologies have the combination of bandwidth, small size, thinness, low cost, durability, sterilizability, or pixelability to work in a small diameter probe.

SUMMARY OF THE INVENTION

The present invention pertains to the design of an optical probe with one or more light delivery channels and one or more light collection channels. The preferred embodiment incorporates one light delivery channel and two light collection channels, wherein one of the collection channels has the same polarization as the delivery channel, and one of the collection channels has a high degree of cross-polarization relative to the delivery channel. Such channels may consist of fiberoptic or other forms or optical waveguides, or of free space optics. The design makes novel use of polarizer technologies that can be "pixelated" at the appropriate size to create "micropolarizers" that can be mounted in a durable and cost-effective fashion at the probe's sample end. Such polarizer technologies include wire grid arrays and nano-crystal films.

This invention features a variably-polarizing optical probe assembly. The assembly comprises an optical probe having one or more optical light delivery channels that emit incident light from the sample end of the probe toward a sample being investigated, and one or more optical light-receiving channels that receive incident light from the sample. The assembly further comprises a polarizing substrate assembly, which itself comprises an optically transmitting substrate and one or more discrete polarizer areas on a face of the substrate, each such polarizer area defining a polarization orientation, with the polarizer areas together preferably defining at least two different polarization orientations. The substrate assembly is coupled to the sample end of the probe such that one polarizer area covers at least one light delivery channel and a different polarizer area covers at least one light-receiving channel.

The polarizer areas may comprise wire grid array polarizers or dichroic polarizers formed with nano crystals. The substrate assembly is preferably less than about 200 microns thick, and may have a high efficiency anti-reflection coating on the sample side to minimize Fresnel reflections. The polarizer may be optimized for ultraviolet, visible, infrared, or another wavelength or combination of wavelengths in the electromagnetic spectrum. This is accomplished in the case of wire grid array polarizers by adjusting the width, height, and/or spacing of the wires. This is accomplished in the case of nano-crystal polarizers through the choice of materials and processing parameters such as temperature. The optical channels may be optimized for ultraviolet, visible, infrared, or another wavelength or combination of wavelengths in the electromagnetic spectrum. In the case of fiberoptic channels, this is accomplished by the choice of materials, dopants, and core/clad ratios. For other kinds of optical channels, this is accomplished by the choice of materials and the design of any optical coatings used in the channels.

The substrate may be formed from a scratch-resistant material such as quartz, fused silica, or sapphire. The substrate assembly may have a diamond-like, rhodium or other hard coating on its sample side to increase its scratch resistance. The substrate may be made of glass or polymer that transmits broadband radiation, does not substantially fluoresce, does not impart significant birefringence, and is biocompatible.

Two of the polarizer areas may have orthogonal polarization orientations. The optical probe may comprise at least two discrete light-receiving channels, with one polarizer area covering at least one light-receiving channel and a second, orthogonally-oriented polarizer area covering at least one light delivery channel and at least one light-receiving channel. The optical probe may comprise at least three discrete light-receiving channels, with one polarizer area covering at least two light-receiving channel and a second, orthogonally-oriented polarizer area covering at least one light delivery channel and at least one light-receiving channel. At least two light-receiving channels may be substantially tangent to a light delivery channel, or may be separated by certain distances that determine a sampling geometry, i.e., determine a specific volume of the sample from which scattered or reflected light is collected.

The polarizer areas may be substantially circular, and may be substantially tangent to one another. The sample end of the probe may be substantially circular, and the polarizer areas may be substantially tangent to the edge of the probe's sample end. The polarizer areas may be substantially aligned with one another. The substrate assembly may further comprise a non-polarized buffer zone separating at least two polarizer areas from one another. The buffer zone may divide the substrate assembly into two discrete portions.

This invention also features a variably-polarizing substrate assembly for polarizing the incident light emitted from the sample end of one or more light delivery channels of an optical probe, and the light received into one or more light-receiving channels of the optical probe, the assembly comprising an optically transmitting substrate and at least two discrete polarizer areas on a face of the substrate, each such polarizer area defining a polarization orientation, with the polarizer areas together defining at least two different polarization orientations.

Further featured in the invention is a variably-polarizing substrate assembly for polarizing the light received by or emitted from a device, comprising an optically transmitting substrate and at least two discrete polarizer areas on a face of the substrate, each such polarizer area defining a polarization orientation, with the polarizer areas together defining at least two different polarization orientations. The device may comprise an image sensor, to accomplish polarized imaging with a single image sensor.

BRIEF DESCRIPTION OF THE DRAWINGS

Other objects, features and advantages will occur to those skilled in the art from the following description of the preferred embodiments and the accompanying drawings in which.

DETAILED DESCRIPTION OF THE PREFERRED EMBODIMENTS OF THE INVENTION

Figure 1:
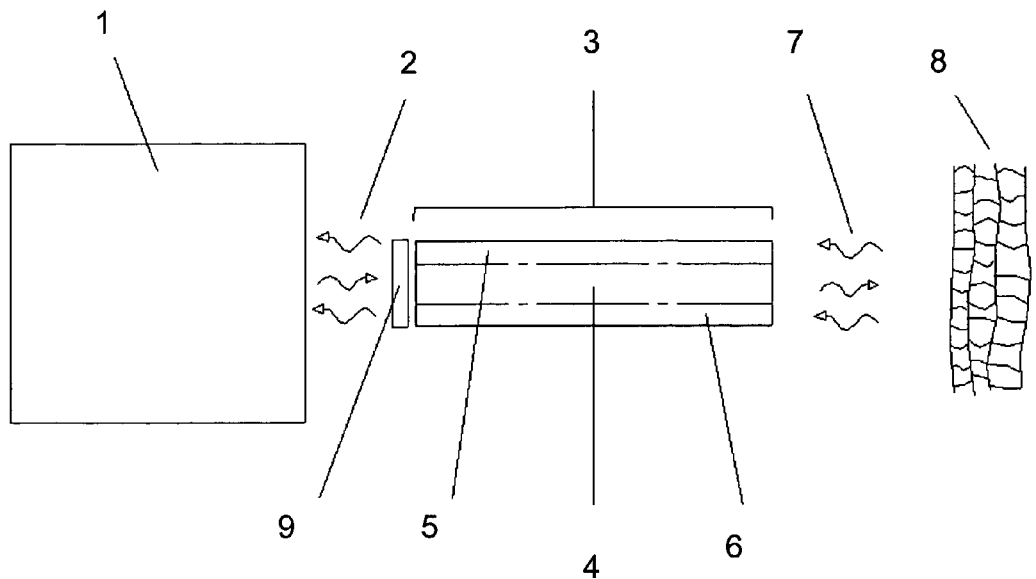
FIG. 1 is a schematic diagram of a prior art optical probe, in which polarizers are placed between the probe and an analysis instrument.
Figure 2:
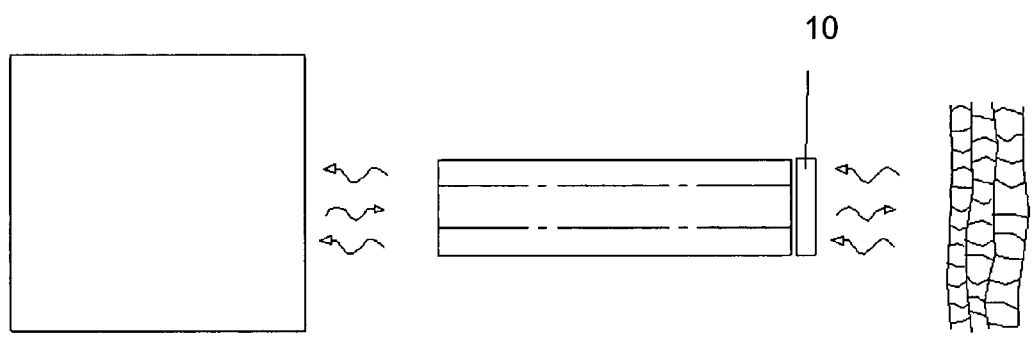
FIG. 2 is a schematic diagram of a preferred embodiment of the invention.

An embodiment of the present invention is shown schematically in FIG. 2. Pixelated variably-polarizing substrate assembly 10 is placed at the sample end of probe 3. Substrate assembly 10 has one or more discrete polarized areas defining particular polarization orientations, each such area (called a "pixel" herein) defining a single polarization axis. In most applications in which there are two pixels, the polarization axes of the pixels will be orthogonal with respect to one another. The pixels are sized, shaped and located to correspond to the size, shape and location at the probe sample end of the optical channels of the probe. Pixelated substrate assembly 10 has a thickness that results in an acceptable level of Fresnel reflections in small diameter probes (defined as probes with a distal tip diameter of less than 25 mm, and preferably less than about 10 mm). Typically, pixelated substrate assembly 10 is no more than about 200 microns thick.

This invention accomplishes the creation of patterns of polarizer "pixels" that can have any polarization orientation. These pixel patterns are compatible with the wire grid fabrication process. They are also designed to make alignment to probe optical channels easy, cost-effective, and adaptable to a variety of probe configurations.

Figure 3:
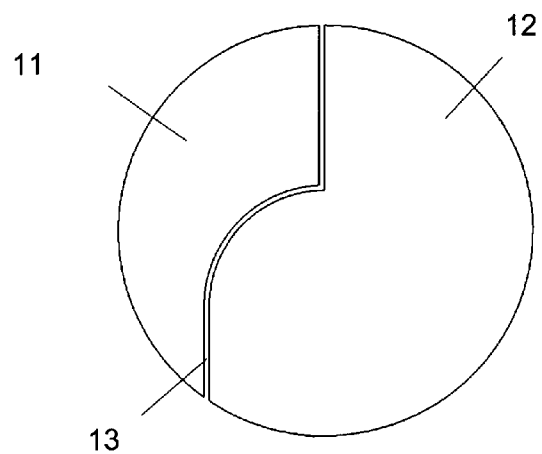
FIGS. 3–8 are schematic diagrams of alternative preferred substrate assemblies for the invention.
Figure 4:
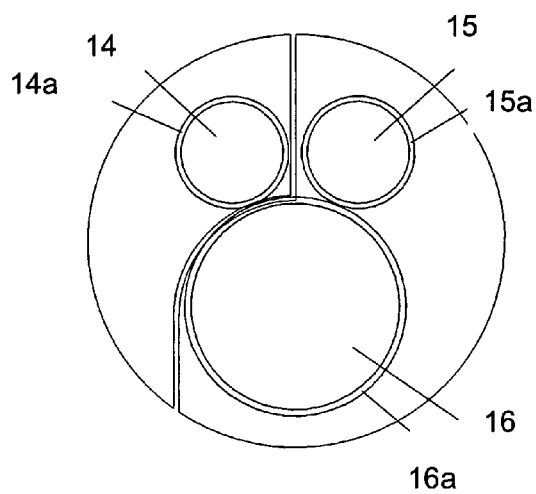

FIGS. 3 through 6 show a preferred exemplary embodiment of a pixelated substrate for this invention, showing a pixel pattern and its relationship to 3 optical channels. This pattern is optimized for use with one large delivery channel and two smaller collection channels. As shown in FIG. 3, the pattern consists of two pixels: the cross-polarized pixel 11 and the parallel-polarized pixel 12. As shown in FIG. 4, pixel 11 is designed to cover a single optical detection channel 14, while pixel 12 is designed to cover the other detection channel 15 and the delivery channel 16. In FIGS. 3 through 6 the optical channels are shown as optical fibers, with cores 14, 15 and 16 and outer cladding 14a, 15a and 16a, respectively. The optical channels could alternatively be formed from non-clad optical waveguides, or free space optics. When clad fiberoptics are not used, 14, 15 and 16 represent the clear apertures of the channels, and 14a, 15a, and 16a (if present) represent space between the channels. To optimize signal-to-noise, each collection channel is substantially tangent to the delivery channel. The two collection channels need not be tangent to each other.

Figure 5:
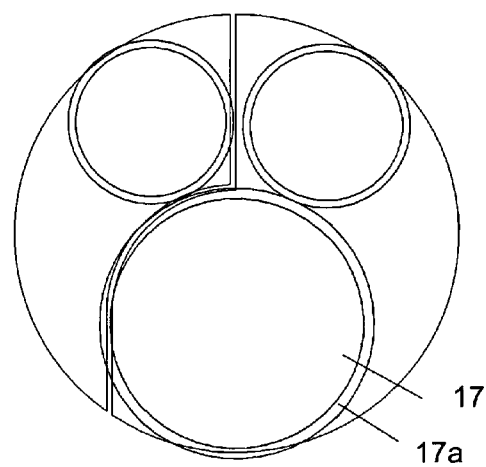
Figure 6:
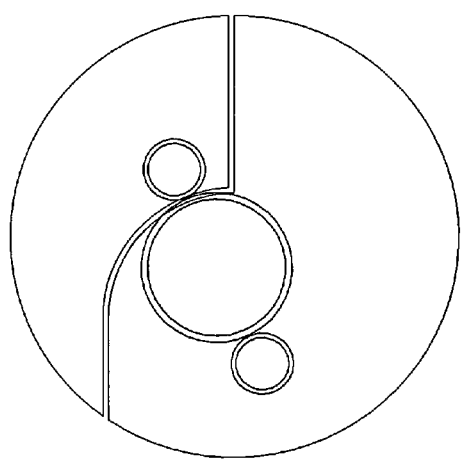

In the lithographic polarizer pixel production technique that is preferably used to create the wire grid array polarizer pixels, inherent alignment errors between successive masks can be accounted for by spacing the pixels slightly with what is called a "buffer zone" (a non-polarized area between pixels). The buffer zone may divide the substrate face in two. Advantageously, the pixels' borders can be placed so that these buffer zones lie over non-active areas of the probe face. For example, the pixel pattern can be arranged so that the buffer zone 13 (FIG. 3) lies between each of the fiber cores if optical fibers are used (or clear apertures of non-clad optical channels). Light emitted from optical channel 16 passes through the polarizer and is linearly polarized with an orientation that is arbitrarily called "parallel". This light irradiates the sample. Backscattered rays are collected by the two detection channels 14 and 15. Channel 15 collects rays with the same orientation as the irradiating light while channel 15 collects rays with orthogonal polarization. The optical channels shown in FIG. 4 are of a typical size for this pixel pattern. FIG. 5 shows optical channels of the largest possible size for this pattern and a circular probe end. Note that all of the pixels in this case are substantially tangent to the perimeter of the probe in order to maximize the number of polarizers that may be patterned in a lithographic fabrication mask. As long as the fiber core 17 is completely covered by the pixel, the cladding 17a may fall outside the pixel. FIG. 6 shows that the same pattern used with arbitrarily small channels. In FIGS. 4 through 6, the pixel pattern is arranged so that the collection channels 14 and 15 are substantially tangent with the delivery channel 16, and so that the buffer zone 13 overlays either the cladding, if the channels are fiberoptic, or between the clear apertures of the channels if non-clad waveguides or free space optics are used. Thus, this embodiment of a pixel pattern is designed to accommodate a substantial range of optical channel sizes. Alternative embodiments of this pixel pattern may be larger or smaller to accommodate a further increased range of optical channels sizes and combinations.

Figure 7:
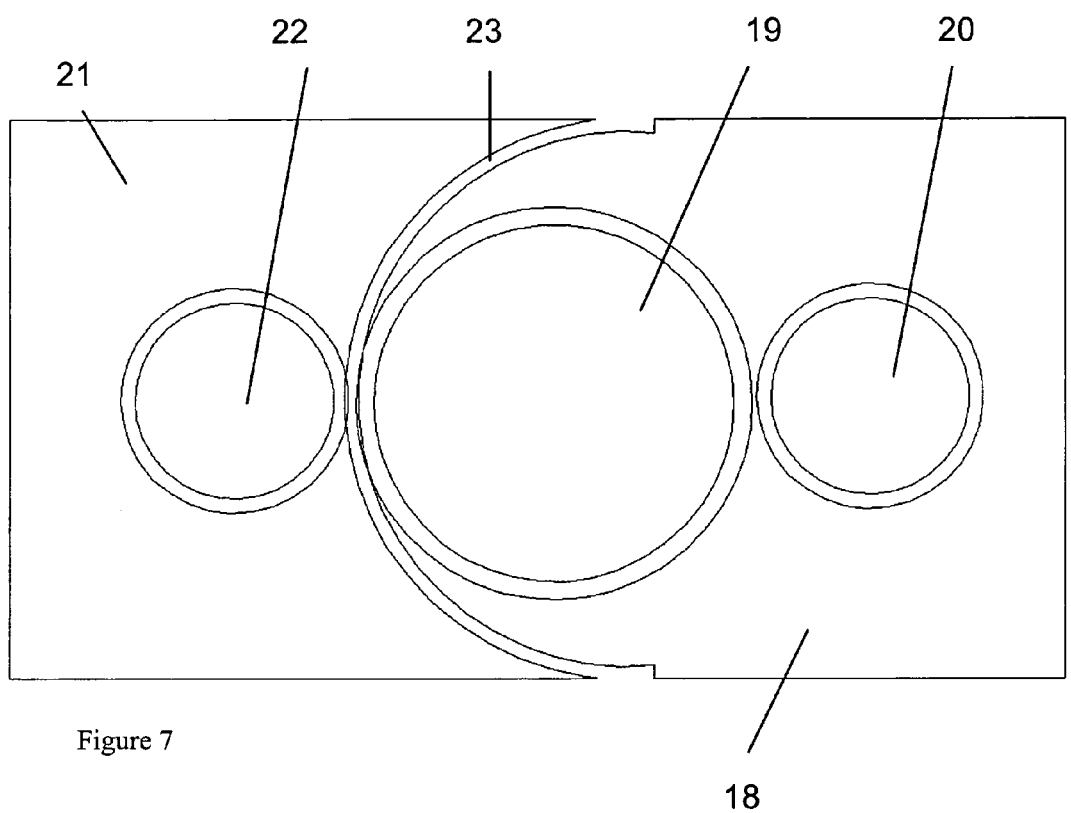
Figure 8:
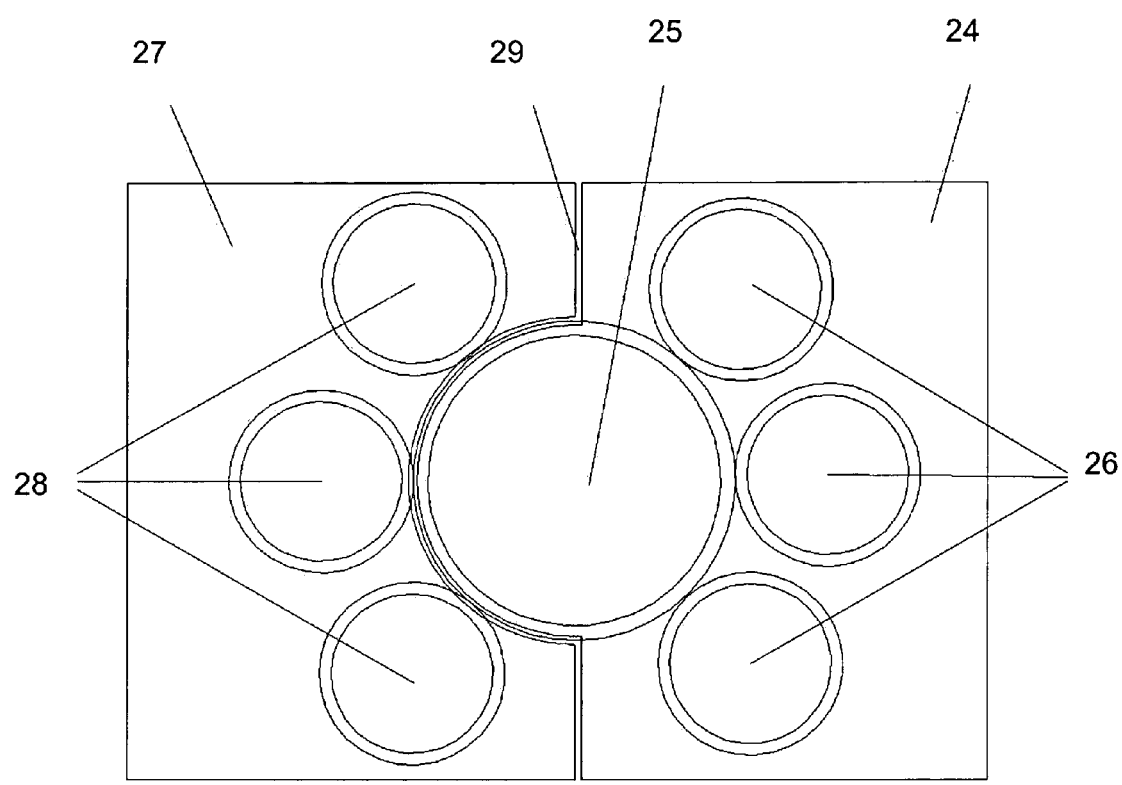

Alternative embodiments incorporate pixels of different shapes than the ones shown in FIGS. 3 through 6. For example, FIG. 7 shows a rectangular pixel pattern placed over three optical channels in a linear arrangement. Parallel polarization pixel 18 covers delivery channel 19 and detection channel 20. Cross polarization pixel 21 covers detection channel 22. Buffer zone 23 is aligned over the cladding areas in the case of clad fiberoptic channels, and between the channel apertures when non-clad waveguides or free space optics are used. This pixel pattern is relatively insensitive to angular misalignment and is thus easier to assemble than other patterns. FIG. 8 shows another alternative embodiment, this one optimized for a central delivery channel 25 surrounded by six substantially concentric collection channels (collectively labeled 26 and 28). Parallel polarization pixel 24 covers the delivery channel 25 and collection fibers 26. Cross polarization pixel 27 covers collection channels 28. A buffer zone 29 is aligned to overlay the inter-channel spaces.

In the embodiments described thus far, each pixel pattern is optimized for probes with certain fixed geometries. However, the shapes of the pixels are designed to accommodate normal assembly tolerances. The optical channels will not always be located at exactly the same places, but as long as the pixel pattern can be rotated in one axis and translated in 2 axes prior to mounting, alignment can be achieve for an acceptable range of assembly tolerances.

The pixelated polarizer substrate assembly of the invention can be fabricated as follows. The substrate comprises a glass that transmits broadband radiation, does not fluoresce, does not impart significant birefringence, and is biocompatible. The glass substrate should be less than about 200 microns thick. The substrate may alternatively be formed from a scratch-resistant material such as quartz, fused silica, or sapphire. The substrate assembly may have a diamond-like, rhodium or other hard coating on its sample side to increase its scratch resistance. The substrate preferably has the same size and shape as the sample end of the probe to which it is coupled (either adhesively or mechanically by clamping or the like). The polarizing pixels are preferably created using the wire grid array technique disclosed in U.S. Pat. No. 6,122,103, the disclosure of which is incorporated herein by reference.

In an alternative embodiment, dichroic polarizers formed with nano crystals are used instead of wire grid arrays. For example, manufacturer Optiva, Inc. has introduced a thinner variant of the sheet polarizer. It is a family of optical films that utilizes what Optiva calls "Thin Crystal Film™ (TCF) nano-material". It allows polarizers to be produced by coating a very thin molecularly-oriented layer film. A high performance polarizer coating results from shear force applied to the liquid as it is applied (i.e., a rolling, brushing, or wiping action). This shear force acts to create a preferred orientation, and "comb" the supramolecular strands created by self-assembly of the crystalline material. After shear force establishes a partial orientation, the liquid crystal property of the strands act to increase alignment. The deposition method produces a uniform polarizing coating of 7 to 15 microns thick when wet. After evaporation of water, a dry, thin crystalline polarizing layer remains with a thickness of 0.5–1 micron. Polarizing sheets of nearly any size may be fabricated. With proper fixturing, this film may be deposited onto substrates as thin as 10 microns. However, because of the requirement to "comb" the supramolecular strands, it is not feasible to create very small, adjacent pixels with orthogonal orientations. Any roller, brush or wiper would need to pass the edge of each pixel in order to orient the strands over the entire area of the pixel. If the pixels are adjacent to each other, the combing action on one pixel disturbs the crystal orientation established on the adjacent pixel. It is therefore necessary to create polarizer sheets that define only one orientation. These sheets are then cut into specific shapes with an automated scribe, laser, e-beam, water jet, or other microcutting technique. Using a vacuum manipulator, these pieces are then oriented onto the sample end of the optical probes. The non-coated side of the pieces are bonded with an optically transparent adhesive to the probe. A UV-curing adhesive provides a nearly instant cure upon application of UV light. Alternatively, other optically transparent one- or two-part adhesives may be used. A cover glass may be fitted to seal the polarizers from environmental exposure.

Alternatively, instead of bonding the pieces directly onto the end of the probe, they may be bonded onto a secondary substrate, and the assembly bonded onto the probe in the same manner. The additional substrate may already be round, or it could be square or some other shape that is easy to form by scribing or dicing. In this case, after bonding to the probe, the substrate is preferably edged round by grinding. A third layer of substrate may also be used, so that the nano-crystal polarizer is "sandwiched" between two protective layers.

Figure 9:
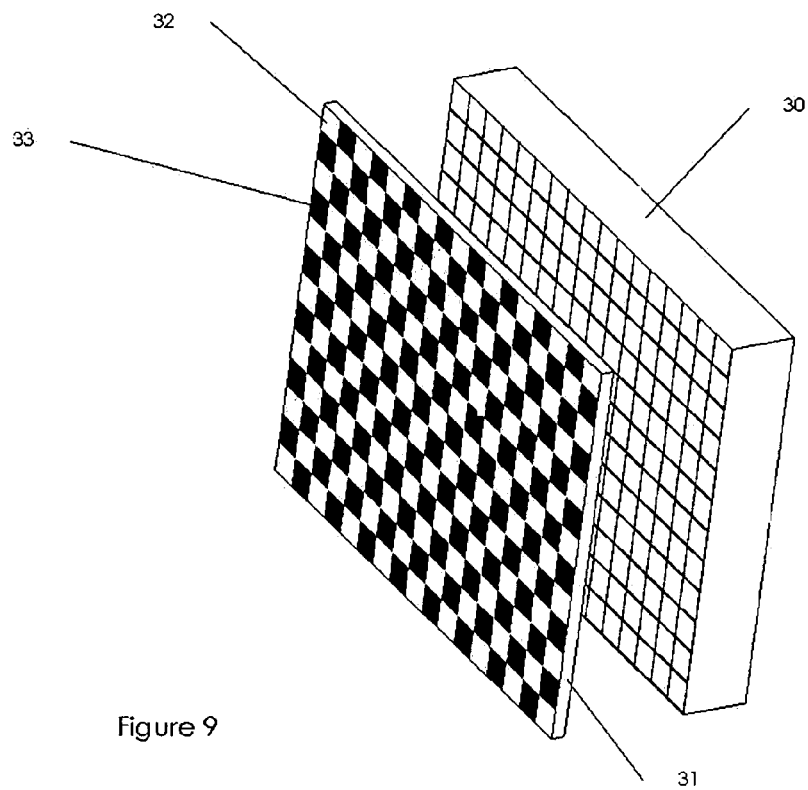
FIG. 9 is a schematic, exploded diagram of a variably-polarizing substrate assembly according to the invention.

The invention also comprises the variably-polarizing substrate assembly per se. This variably-polarizing substrate assembly polarizes the light received by or emitted from a device, for example an image sensor. The substrate assembly comprises an optically transmitting substrate such as described above, and one or more discrete polarizer areas on a face of the substrate, each such polarizer area defining a polarization orientation, with the polarizer areas together preferably defining at least two different polarization orientations. When used with an image sensor, polarized imaging can be accomplished with a single image sensor. FIG. 9 shows a preferred embodiment. A detector array 30 may be comprised of a linear array of pixels or a two-dimensional array as shown. The detector may be a CCD imager, a CMOS imager, a HgCdTe detector, or another type of detector sensitive to some portion of the electromagnetic spectrum. The detector pixels may be contiguous to each other or separated. A polarizer 31 consists of an array of polarizing pixels that matches the size and pitch of the pixels in the detector array. One group of polarizing pixels 32 have one orientation, while another group 33 has a different orientation. The two groups of pixels may be arranged in a checkerboard pattern as shown or in another pattern. For clarity of illustration, the polarizer is shown apart from the detector array. In use, these two components are closely mated.

Figure 10:
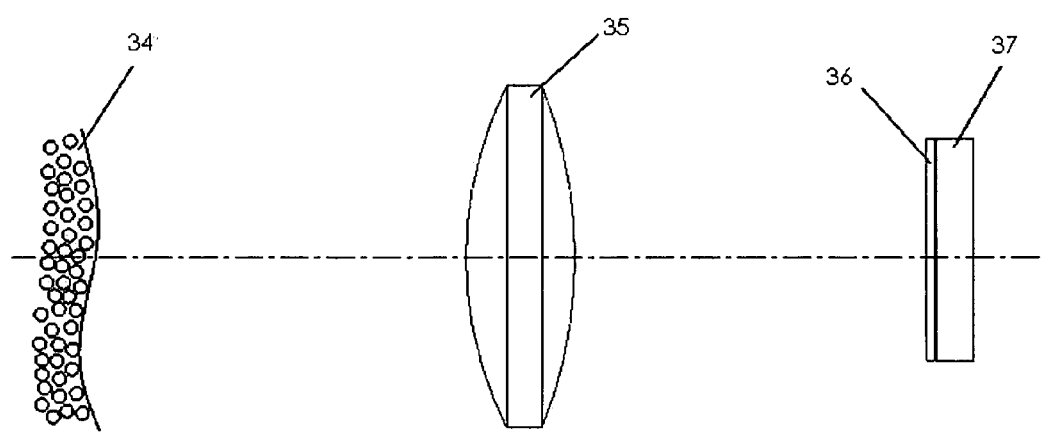
FIG. 10 schematically depicts a variably-polarizing substrate assembly according to the invention in use imaging a sample.

FIG. 10 shows a sample 34 being imaged by a lens 35. The image of the sample passes through polarizer 36, which is shown mounted onto detector 37. The signals from detector array 37 are capable of being processed in such a way that an image may be constructed from one group of pixels separate from the other group of pixels. Thus, images of a sample with different polarization states may be obtained.

What is claimed is:

1. A variably-polarizing optical probe assembly, comprising:
    an optical probe having one or more optical light delivery channels that emit incident light from the sample end of the probe toward a sample being investigated, and one or more optical light-receiving channels that receive incident light from the sample;
    a variably-polarizing substrate assembly, comprising:
        an optically transmitting substrate; and
        one or more discrete polarizer areas on a face of the substrate, each such polarizer area defining a polarization orientation, with the polarizer areas together defining one or more different polarization orientations; and
    means for coupling the substrate assembly to the sample end of the probe such that one polarizer area covers at least one light delivery channel and one polarizer area covers at least one light-receiving channel.

2. The variably-polarizing optical probe of claim 1, wherein the polarizer areas comprise wire grid array polarizers.

3. The variably-polarizing optical probe of claim 1, wherein the polarizer areas comprise dichroic polarizers formed with nano crystals.

4. The variably-polarizing optical probe of claim 1, wherein the substrate assembly is less than about 200 microns thick.

5. The variably-polarizing optical probe of claim 1, wherein substrate assembly has an anti-reflection coating on the sample side to minimize Fresnel reflections.

6. The variably-polarizing optical probe of claim 1, wherein the variably-polarizing substrate assembly is optimized for ultraviolet, visible, infrared, or another wavelength or combination of wavelengths in the electromagnetic spectrum.

7. The variably-polarizing optical probe of claim 1, wherein the optical channels are optimized for ultraviolet, visible, infrared, or another wavelength or combination of wavelengths in the electromagnetic spectrum.

8. The variably-polarizing optical probe of claim 1, wherein the substrate is formed from a scratch-resistant material such as quartz, fused silica, or sapphire.

9. The variably-polarizing optical probe of claim 1, wherein the substrate assembly has a diamond-like, rhodium or other hard coating on its sample side to increase its scratch resistance.

10. The variably-polarizing optical probe of claim 1, wherein the substrate is made of glass or polymer that transmits broadband radiation, does not substantially fluoresce, does not impart significant birefringence and is biocompatible.

11. The variably-polarizing optical probe of claim 1, comprising at least two discrete polarizer areas have orthogonal polarization orientations.

12. The variably-polarizing optical probe of claim 11, wherein the optical probe comprises at least two discrete light-receiving channels, with one polarizer area covering at least one light-receiving channel and a second, orthogonally-oriented polarizer area covering at least one light delivery channel and at least one light-receiving channel.

13. The variably-polarizing optical probe of claim 12, wherein the optical probe comprises at least three discrete light-receiving channels, with one polarizer area covering at least two light-receiving channel and a second, orthogonally-oriented polarizer area covering at least one light delivery channel and at least one light-receiving channel.

14. The variably-polarizing optical probe of claim 12, wherein at least two light-receiving channels are substantially tangent to a light delivery channel.

15. The variably-polarizing optical probe of claim 11, wherein the polarizer areas are substantially aligned with one another.

16. The variably-polarizing optical probe of claim 11, wherein the substrate assembly further comprises a non-polarized buffer zone separating at least two polarizer areas from one another.

17. The variably-polarizing optical probe of claim 16, wherein the buffer zone divides the substrate assembly into two discrete portions.

18. The variably-polarizing optical probe of claim 1, wherein at least one polarizer is substantially circular.

19. The variably-polarizing optical probe of claim 18, wherein at least two of the polarizer areas are substantially circular and substantially tangent to one another.

20. The variably-polarizing optical probe of claim 19, wherein the sample end of the probe is substantially circular, and the polarizer areas are substantially tangent to the edge of the probe's sample end.

* * * * *